(12) United States Patent
Sivaswamy et al.

(10) Patent No.: US 12,135,567 B2
(45) Date of Patent: Nov. 5, 2024

(54) CONTEXT AWARE DYNAMIC POSITIONING OF SENSORS

(71) Applicant: INTERNATIONAL BUSINESS MACHINES CORPORATION, Armonk, NY (US)

(72) Inventors: Hemant Kumar Sivaswamy, Pune (IN); Venkata Vara Prasad Karri, Visakhapatnam (IN); Sarbajit K. Rakshit, Kolkata (IN); Sri Harsha Varada, Vizianagaram (IN)

(73) Assignee: International Business Machines Corporation, Armonk, NY (US)

( * ) Notice: Subject to any disclaimer, the term of this patent is extended or adjusted under 35 U.S.C. 154(b) by 382 days.

(21) Appl. No.: 17/653,668

(22) Filed: Mar. 7, 2022

(65) Prior Publication Data

US 2023/0280769 A1   Sep. 7, 2023

(51) Int. Cl.
 *G05D 1/225* (2024.01)
 *G01W 1/08* (2006.01)
 (Continued)

(52) U.S. Cl.
 CPC .............. *G05D 1/225* (2024.01); *G01W 1/08* (2013.01); *H04W 4/021* (2013.01);
 (Continued)

(58) Field of Classification Search
 None
 See application file for complete search history.

(56) References Cited

U.S. PATENT DOCUMENTS

| 10,028,452 | B2 | 7/2018 | Workman |
| 10,254,442 | B2 | 4/2019 | Cerqueira et al. |
| (Continued) | | | |

FOREIGN PATENT DOCUMENTS

| CN | 113614769 A | 11/2021 |
| CN | 108366531 A | 12/2021 |

OTHER PUBLICATIONS

Mell et al., "The NIST Definition of Cloud Computing", National Institute of Standards and Technology, Special Publication 800-145, Sep. 2011, pp. 1-7.
(Continued)

*Primary Examiner* — Peter D Nolan
*Assistant Examiner* — Michael F Whalen
(74) *Attorney, Agent, or Firm* — Kristofer L. Haggerty

(57) ABSTRACT

A method, a computer program product, and a computer system position a plurality of sensors in an area. The method includes receiving data from the sensors positioned at respective first locations where the data is indicative of weather and environmental parameters. The method includes determining weather conditions and an environmental condition based on the weather and environmental parameters. The method includes determining an impact to the environmental condition by the weather conditions. The method includes determining a second location for the sensors based on the impact to the environmental condition. The sensors are configured to generate further environmental parameters with an increased granular level at the second location. The method includes transmitting instructions to a delivery robot to move the sensors to the second location.

20 Claims, 5 Drawing Sheets

(51) Int. Cl.
  *H04W 4/021*    (2018.01)
  *B64U 101/35*   (2023.01)
  *G01D 21/02*    (2006.01)
  *G01N 33/00*    (2006.01)
  *G01W 1/00*     (2006.01)

(52) U.S. Cl.
  CPC ......... *B64U 2101/35* (2023.01); *G01D 21/02* (2013.01); *G01N 33/0075* (2013.01); *G01W 2001/006* (2013.01)

(56) References Cited

U.S. PATENT DOCUMENTS

| | | |
|---|---|---|
| 2016/0298306 A1 | 10/2016 | De Kontz |
| 2016/0299511 A1 | 10/2016 | De Kontz |
| 2018/0313976 A1* | 11/2018 | Cerqueira ............... G01W 1/02 |
| 2018/0368338 A1 | 12/2018 | Jerphagnon |
| 2020/0387419 A1 | 12/2020 | Yang |
| 2023/0069833 A1* | 3/2023 | Frey ........................ G01W 1/02 |

OTHER PUBLICATIONS

PCT International Searching Authority, "Notification of Transmittal of the International Search Report and the Written Opinion of the International Searching Authority, or the Declaration", Date of Mailing Apr. 21, 2023, International Application No. PCT/CN2023/075347, 7 pgs.

\* cited by examiner

CONTEXT AWARE DYNAMIC POSITIONING OF SENSORS

BACKGROUND

The exemplary embodiments relate generally to sensors, and more particularly to positioning of the sensors at strategic locations in a dynamic manner to perform surrounding control of an area.

An area may have surroundings that experience various types of conditions. For example, the surroundings may experience weather conditions such as temperature, humidity, wind, light, etc. The surroundings may also experience environmental conditions such as dust, pollution, pollen, etc. The weather conditions and the environmental conditions may impact the surroundings in various ways. Thus, the area may incorporate one or more control operations that may be applied in the surroundings to address the weather and environmental conditions. However, to apply the appropriate control operation, the weather conditions and the environmental conditions must be determined accurately or the control operation may not properly address the weather conditions and environmental conditions.

SUMMARY

The exemplary embodiments disclose a method, a computer program product, and a computer system for positioning a plurality of sensors in an area. The method comprises receiving data from the sensors that are each positioned at a respective first location. The data is indicative of weather parameters and environmental parameters. The method comprises determining weather conditions and an environmental condition of the area based on the weather parameters and the environmental parameters. The method comprises determining an impact to the environmental condition by the weather conditions. The method comprises determining a second location for at least one of the sensors based on the impact to the environmental condition so that the environmental condition in the area is controlled. The at least one sensor is configured to generate further environmental parameters with an increased granular level at the second location. The method comprises transmitting instructions to a delivery robot to move the at least one of the sensors to the second location.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
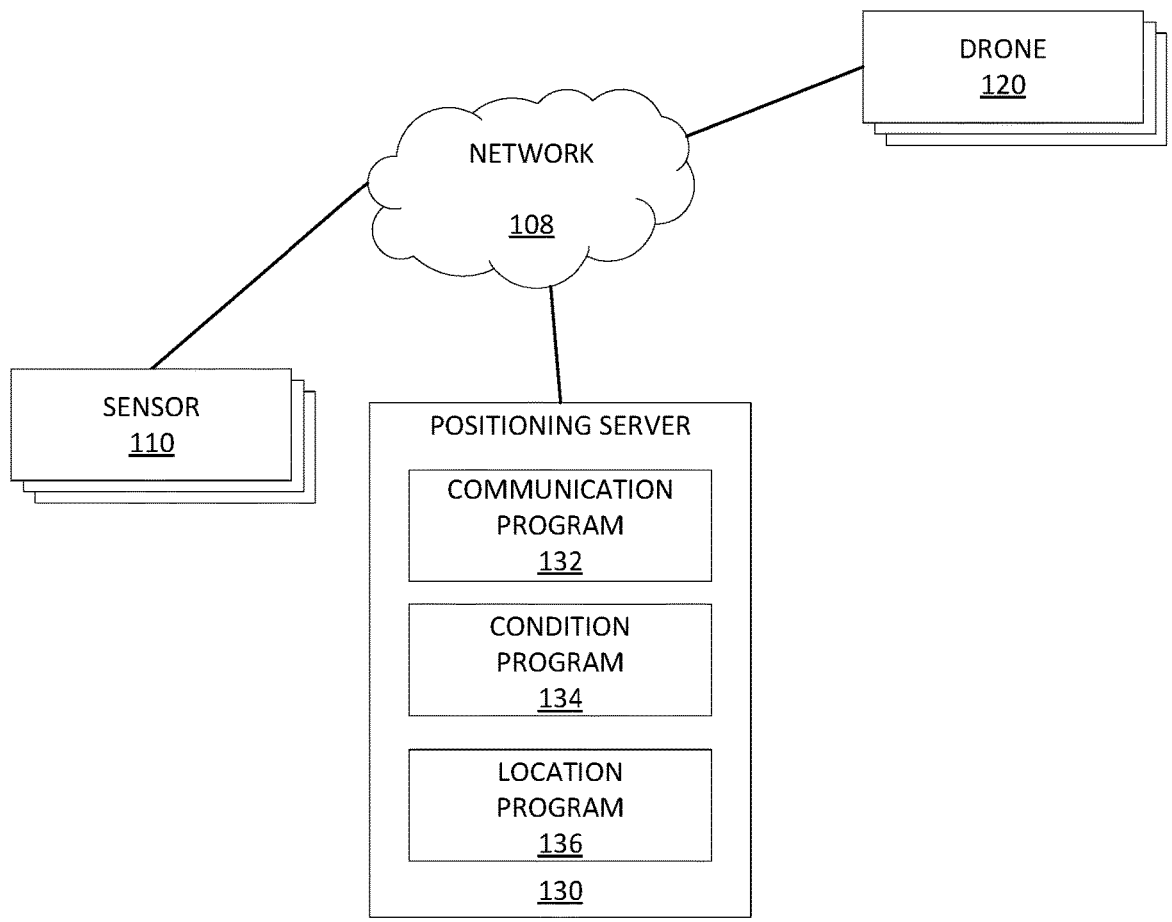
FIG. 1 depicts an exemplary schematic diagram of a sensor positioning system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

The exemplary embodiments are directed to a method, computer program product, and system for positioning a plurality of sensors in an area. The exemplary embodiments provide a mechanism that determines weather conditions and environmental conditions based on weather parameters and environmental parameters, respectively, as measured by strategically positioned sensors. The exemplary embodiments may determine a manner in which one type of the conditions may affect the other type of the conditions. Based on these results, the exemplary embodiments may determine a proper location in which to position the sensors to measure the parameters with greater accuracy. In this manner, the exemplary embodiments may provide valuable input to a control operation that may affect how to address the weather and/or environmental conditions. Key benefits of the exemplary embodiments may include controlling the area very precisely by capturing the environmental and weather parameters in a very granular manner by properly positioning the sensors with an optimum deployment. Detailed implementation of the exemplary embodiments follows.

Conventional approaches have been proposed to utilize and place sensors to measure various conditions. For example, a conventional approach recommends a number of dedicated sensors to be deployed as well as a formation for the dedicated sensors based on dynamic local conditions derived using meteorological data, demographic data, incident data, agricultural data, infrastructure data, weather data, and environment data. In another example, a conventional approach automatically generates recommendations to optimize a placement of sensors on a field by collecting and analyzing a multitude of data such as multispectral imagery, soil maps, weather data, pump data, and environmental factors in real-time as well as updating the placements based on updates in the multitude of data. In a further example, a conventional approach determines an optimal placement of sensors in a field to form a sensor network by performing one or more iterations of a genetic algorithm (GA) routine using an initial set of the plurality of potential placement points until a termination condition is satisfied. In yet another example, a conventional approach dynamically positions sensors to observe plants and adaptively changes a positioning of the sensors based on weather data and environmental factors determined in real-time by a horticultural monitor. However, in each of these conventional approaches, the sensors are geared toward a specific purpose where the sensors are measured using data directed to that purpose (e.g., meteorological data, topological data, etc.). These conventional approaches therefore are only configured to provide data for that specific purpose. In their entirety, the conventional approaches do not describe an application of controls that are used in a precise manner based on environmental conditions that may be affected by weather conditions at a given time where the positioning of the sensors is determined dynamically for this objective so that the environmental conditions may be addressed.

The exemplary embodiments provide a mechanism to precisely control an area by basing the control operation on weather and environmental conditions measured by sensors that are strategically placed in the area for this particular objective. In this manner, the sensors provide significantly relevant and accurate information with regard to the weather and environmental conditions being experienced by the area. To control any area in a very precise manner, the sensors need to capture the weather and environmental parameters used to determine the weather and environmental conditions in a very granular manner. Thus, the exemplary embodiments incorporate a manner of properly positioning the sensors that has great importance in determining the correct control operation to be performed in the area. For example, an area may be described as an agricultural land, a safe home, a health care surrounding, etc. Accordingly, the control operation may be used to reduce, minimize, or prevent a particular severity of an environmental condition from being experienced in the area. However, again, the sensors must measure the weather and environmental parameters with increased accuracy for the weather and environmental conditions to be determined. There may also be a correlation between the weather and environmental conditions such as the weather parameter related to a wind factor may impact the environmental parameter associated with a concentration of airborne particulates such as pollution, dust, pollen, etc. In addition, different types of sensors are required to measure different types of parameters. Deploying all the various types of sensors at all possible locations in the area results in poor efficacy and high costs. In this manner, the exemplary embodiments determine an optimization solution that defines an optimum deployment of the sensors in an area, so that the area may be controlled effectively through one or more control operations.

The exemplary embodiments are described with particular reference to the weather conditions impacting the environmental conditions. As one skilled in the art will understand, the weather conditions may impact the environmental conditions with a more immediate effect (e.g., wind blows pollen from one part of the area to another part of the area in a relatively short period of time). However, the exemplary embodiments being directed to the weather conditions impacting the environmental conditions is only for illustrative purposes. The exemplary embodiments may also be utilized to determine an appropriate control operation based on how the environmental conditions affect the weather conditions. Accordingly, the exemplary embodiments describing the positioning of sensors based on weather conditions that impact environmental conditions may represent any manner in which the exemplary embodiments may be implemented.

FIG. 1 depicts an exemplary schematic diagram of a sensor positioning system 100, in accordance with the exemplary embodiments. According to the exemplary embodiments, the sensor positioning system 100 may be for an area and may include one or more sensors 110, one or more drones 120, and a positioning server 130, which may all be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the area may represent any geographical area. The area may be of any size from a room to a city or even smaller/larger areas. However, those skilled in the art will appreciate that the area may be of a sufficient size to warrant the implementation of the exemplary embodiments (e.g., based on a cost analysis). The area may also include one or more sites that may require the use of control operations to address various environmental conditions. For example, the area may include a health care facility to treat health related conditions. Accordingly, the area may utilize one or more control operations to reduce, minimize, or prevent adverse environmental conditions or a severity thereof associated with the health related conditions. In another example, the area may include a home of an individual who has a pollen sensitivity. Accordingly, the area may utilize one or more control operations to minimize or reduce the pollen concentration in proximity to or within the home.

The exemplary embodiments are described with regard to implementing control operations. The exemplary embodiments may be utilized in determining a plurality of different types of control operations that may be applied to the area. As the control operations may be based on the type of area or a part thereof, the exemplary embodiments may utilize the area or a part thereof as an input in determining the positioning of the sensors 110. For example, as noted above, individuals in the area may be sensitive to a particular environmental condition. Accordingly, the control operations may be applied to the area to minimize or reduce the impact of the environmental condition on the individuals of the area (e.g., increase or activate filtering of air to reduce pollen concentration in a building located in the area, increase a shading on windows to reduce high temperature or light exposure in the area, close windows to prevent particulates from entering a building, etc.). The control operations may be tasks performed automatically by a system that is in place within the area. The control operations may also be manual tasks performed by individuals based on a recommendation generated by the exemplary embodiments. In this manner, the exemplary embodiments may be associated with any type of control operation that may be applied to the area as a result of determining the environmental conditions that may be impacted by the weather conditions. That is, the area providing an input (e.g., objective of control for the area via the control operation) to the process of determining the positioning of the sensors 110 may therefore also determine the control operation to be applied to the area. Therefore, the area may be described as utilizing a control operation to represent controlling an environmental condition that is to be experienced at the area or a portion thereof.

In the exemplary embodiments, the network 108 may be a communication channel capable of transferring data between connected devices. Accordingly, the components of the sensor positioning system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices. For example, the network 108 may also represent direct or indirect wired or wireless connections between the components of the sensor positioning system 100 that do not utilize the network 108. In a particular implementation, the network 108 may be a closed network (e.g., an intranet) that allows the components of the sensor positioning system 100 to communicate with one another. The network 108 being a closed network may still allow components of the sensor positioning system 100 to maintain a communication pathway regardless of a location in the area.

In the exemplary embodiments, the sensors 110 may be any device configured to measure a parameter. As noted above, the area may experience a plurality of different weather conditions and a plurality of different environmental conditions. As the exemplary embodiments may utilize a plurality of different weather and environmental conditions, the exemplary embodiments may also incorporate a variety of types for the sensors 110 configured to measure parameters to determine corresponding ones of the weather and environmental conditions. The types of the sensors 110 may be based on, for example, the area being monitored, an objective to be achieved for the area, another characteristic of the area, an unrelated objective, or a combination thereof. The sensors 110 may also be reusable sensors that may be used to measure selected types of weather and/or environmental parameters.

The sensors 110 may measure one or more parameters from which the exemplary embodiments may determine the weather and environmental conditions. According to the exemplary embodiments, the sensors 110 may include weather sensors that measure parameters related to weather conditions. For example, the weather sensors may measure weather parameters such as temperature, humidity, wind flow, light, precipitation, etc. Accordingly, as one skilled in the art will understand, the sensors 110 may incorporate components configured to measure one or more of these weather parameters. According to the exemplary embodiments, the sensors 110 may also include environmental sensors that measure parameters related to environmental conditions. For example, the environmental sensors may measure environmental parameters such as smell, dust, pollution, pollen, air quality, etc. Accordingly, as one skilled in the art will understand, the sensors 110 may incorporate components configured to measure one or more of these environmental parameters.

The exemplary embodiments measure weather parameters and environmental parameters to determine the weather conditions and the environmental parameters at a significantly granular level. Accordingly, when placed, the sensors 110 may be substantially near a surface (e.g., a ground level, a level in which an individual may be located, etc.) in the area. In this manner, the sensors 110 may take readings for a portion of the area where an individual may experience the weather and environmental conditions.

The sensors 110 may also be positioned in various locations to measure weather parameters and environmental parameters. For example, the sensors 110 may be positioned within the area to take measurements of the parameters. In this manner, the sensors 110 may make direct measurements of weather and environmental parameters for the area based on measurements made in the area. In another example, the sensors 110 may be positioned in proximity to but outside the area to take measurements of the parameters. As will be described in further detail below, the weather conditions may impact the environmental conditions. This impact to the environmental conditions at a specific portion of the area may not necessarily be from experiencing the weather condition at that same specific portion of the area. Instead, a weather condition being experienced at a first portion of the area may impact an environmental condition in a second portion of the area. In this manner, the sensors 110 may make indirect measurements of weather and environmental parameters for the area based on measurements made outside the area. In a further example, the sensors 110 may be positioned within and outside the area to generate a more thorough understanding of the weather and environmental conditions for the area in a combination manner.

In the exemplary embodiments, the drones 120 may be one or more unmanned aerial vehicles (UAVs) configured with a load carrying device as well as an air movement device. For example, each of the drones 120 may be equipped with components (e.g., articulating arms, a carriage, etc.) configured to collect one of the sensors 110 for subsequent placement at a determined location in the area. In another example, each of the drones 120 may be equipped with a flight device (e.g., one or more propellers having one or more blades), an engine (e.g., to actuate the flight device), a power supply (e.g., a battery to provide electrical energy to the engine), etc. The drones 120 may also be configured with a processor, a location device, etc. The processor may be configured to control the movement of the drone 120 based on instructions that are received. The location device may be a GPS, a triangulation component, a signal processing device (e.g., RSSI), etc. to determine a geographic location of the drone 120, determine a flight path to reach a destination corresponding to the determined location in which to place the collected one of the sensors 110. The drones 120 may further be configured with a communication device. For example, the drones 120 may each include a transceiver configured to wirelessly exchange data (e.g., to receive instructions in repositioning one of the sensors 110).

The exemplary embodiments are described with regard to utilizing the drones 120 to reposition the sensors 110 based on determined locations for the sensors 110. One skilled in the art will understand that a versatility that the drones 120 may provide. The drones 120 may also be incorporated into an automated system to automatically determine and reposition the sensors 110. However, the use of the drones 120 is only for illustrative purposes. The exemplary embodiments may utilize any type of delivery robot/device or manner of repositioning the sensors 110. For example, other automated delivery devices (e.g., ground transportation devices) may be used. In another example, the exemplary embodiments may generate instructions or recommendations to reposition the sensors from which the sensors 110 may be manually repositioned. In this manner, the drones 120 may represent any manner in which to reposition the sensors 110 based on a location determined using the exemplary embodiments.

In the exemplary embodiments, the positioning server 130 may include a communication program 132, a condition program 134, and a location program 136, and be in a communicative relationship with the delivery arrangement 110 and the drones 120. The positioning server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the positioning server 130 is shown as a single device, in other embodiments, the positioning server 130 may be comprised of a cluster or plurality of computing devices, working together or working independently. The positioning server 130 is described in greater detail as a hardware implementation with reference to FIG. 3 (e.g., data processing according to the exemplary embodiments being performed by processor 02), as part of a cloud implementation with reference to FIG. 4 (e.g., the positioning server 130 according to the exemplary embodiments being represented by the desktop computer 54B), and/or as utilizing functional abstraction layers for processing with reference to FIG. 5 (e.g., workload layer 90 including position processing 96 according to the exemplary embodiments).

In the exemplary embodiments, the communication program 132 may be a software, hardware, and/or firmware application configured to exchange data with the sensors 110 and the drones 120. For example, the communication program 132 may exchange data with the sensors 110 to receive data associated with weather parameters and environmental parameters. In another example, the communication program 132 may exchange data with the drones 120 to provide instructions.

In the exemplary embodiments, the condition program 134 may be a software, hardware, and/or firmware application configured to utilize the data from the sensors 110 including the data associated with the weather parameters and the environmental parameters to determine weather conditions and environmental conditions. For example, the sensors 110 may include a weather sensor such as a thermometer that measures a heat value from which the condition program 134 may determine the weather condition of a temperature for a portion of the area in which the thermometer is located. In another example, the sensors 110 may include an environmental sensor such as a particle sensor that measures a number of various types of particles in the air such as dust, pollen, etc. from which the condition program 134 may determine an environmental condition of a concentration of that particle for a portion of the area in which the particle sensor is located. In a further example, the sensors 110 may include a weather sensor such as an anemometer that measures a wind speed, a wind direction, a wind pressure, etc. from which the condition program 134 may determine a weather condition of wind conditions for a portion of the area in which the anemometer is located. In this manner, the condition program 134 may process the environmental and weather parameters to determine corresponding environmental and weather conditions.

The condition program 134 may further be configured to determine how the weather conditions impact the environmental conditions. For example, wind conditions in a first portion of the area (e.g., as measured by a sensor 110 located within the area) or outside the area (e.g., as measured by a sensor 110 located outside the area) may cause particles in the air to move to a second portion of the area where the second portion of the area is downwind of the first portion of the area. Accordingly, the condition program 134 may predict that the second portion of the area will experience the environmental condition of a greater concentration of an identified air particle.

The condition program 134 may be trained using various techniques such as modeling techniques, artificial intelligence, machine learning, etc. and utilize neural networks (e.g., RNN, CNN, etc.) that utilize training data that may include historical data for various weather and environmental conditions that were experienced in the area or in other areas. The condition program 134 may be configured to gather or have access to historical weather parameters and historical environmental parameters as well as the corresponding historical weather conditions and historical environmental conditions for the area (e.g., as stored in a data repository (not shown)). The condition program 134 may utilize the historical information to determine and/or predict different types of environmental and weather conditions under current environmental and weather parameters measured by the sensors 110 through the one or more training techniques employed in generating models. The condition program 134 may also utilize the historical information to determine and/or predict correlations between the weather conditions and the environmental conditions also based on the one or more training techniques employed in generating the models. The correlations may be directed to a manner in which weather conditions may control and/or impact environmental conditions (e.g., wind flow direction may control movement of air particles such as pollen, smell, etc.). The condition program 134 may utilize a knowledge corpus about the correlations of various weather parameters and weather conditions influencing environmental parameters and environmental conditions, or vice versa. The condition program 134 may further utilize the historical information to determine assumptions when the current parameters may lack sufficient information. For example, at certain times of the year, the pollen concentration at a given portion of the area may historically be observed to fall within a range.

The condition program 134 may be configured to provide an initial set of results for subsequent processing (e.g., to determine how to position the sensors 110). For example, based on a current positioning of the sensors 110, the condition program 134 may receive measurements for weather parameters and environmental parameters to determine the corresponding weather conditions and environmental conditions. Accordingly, the condition program 134 may analyze initial sensor feed about the area.

In the exemplary embodiments, the location program 136 may be a software, hardware, and/or firmware application configured to determine how to position the sensors 110 to monitor the weather conditions and the environmental conditions based on the results of the condition program 134. The location program 136 may also be configured to select the appropriate type of the sensors 110 and position these types of sensors 110 at determined locations. The location program 136 may utilize historical information, various learning techniques with corresponding models, the knowledge corpus, etc. to determine how to position the sensors 110 have a determined type. Accordingly, the location program 136 may determine how to place a specific type of the sensors 110 to monitor a corresponding weather condition and/or environmental condition.

As described above, the condition program 134 may analyze an initial sensor feed about the area. Based on these results, the location program 136 may use the initial sensor feed as an input to make a plurality of determinations. For example, the location program 136 may determine the types of sensors 110 that may be required based on the initial sensor feed from the sensors 110 at their current positions. In another example, the location program 136 may determine where to position the determined types of sensors 110 so that the weather parameters and the environmental parameters may be measured at a very granular level to increase an accuracy with which the area is actually experiencing the weather and environmental parameters.

In an exemplary scenario, the condition program 134 may have analyzed the initial sensor feed for the area based on measurements of weather parameters and environmental parameters from the sensors 110 according to their current locations. The condition program 134 may thereby determine corresponding weather conditions and corresponding environmental conditions. Based on these results, the condition program 134 may have determined that there is an environmental condition in which there is a concentration of pollen in a first portion of the area. The condition program 134 may have also determined that there is a weather condition in which wind having an identified speed and direction is being experienced in the first portion of the area. The condition program 134 may also determine or predict that the environmental condition in the first portion of the area is likely to be experienced in a second portion of the area based on the weather condition directed to the wind. The condition program 134 may also incorporate other available information such as topology information, interference information (e.g., trees, buildings, etc. that may be in the path of the wind), etc. The location program 136 may receive these results from the condition program 134 to determine that the sensors 110 to be deployed is to include a pollen sensor and that the pollen sensor is to be positioned to measure the pollen in the second portion of the area. Thus, in this exemplary scenario, based on the weather conditions, the exemplary embodiments may identify where and how many sensors 110 configured to measure the appropriate environmental parameters are to be strategically placed in the area. In this manner, the condition program 134 and the location program 136 may cooperatively determine which of the sensors 110 to be used and how to position these sensors 110 in the area.

As a result of determining the types of the sensors 110 and the corresponding locations in which to position the sensors 110, the exemplary embodiments may apply any changes to the area. For example, the positioning server 130 may generate instructions that are transmitted to the drones 120 indicating which of the sensors 110 are to be repositioned to an updated location. The drones 120 may collect and deliver the sensors 110 that are spaced in the area based on the instructions of the locations that the sensors 110 are to be positioned to capture the required information regarding the weather parameters and environmental parameters being experienced at the location the sensors 110 is placed.

Once placed in the determined locations, the positioning server 130 may continue to monitor the weather conditions and the environmental conditions. For example, the positioning server 130 may receive information from the sensors 110 that are now placed in the determined locations. The information being received may correspond to the initial sensor feed that was used in the previous iteration of determining the current locations of the sensors 110. In this manner, the positioning server 130 may continuously determine modifications to the positioning of the sensors 110 and may identify any additional changes given the contextual situation of the area.

By repositioning the sensors 110 appropriately based on the weather conditions and the environmental conditions, the positioning server 130 may determine a manner in which to utilize control operations. As described above, the control operations may reduce an influence that the weather conditions and the environmental conditions may exhibit on the area. With the weather conditions and the environmental conditions being monitored through gathering weather parameters and environmental parameters at a very granular level, the control operations may be selected and applied with optimal results.

Figure 2:
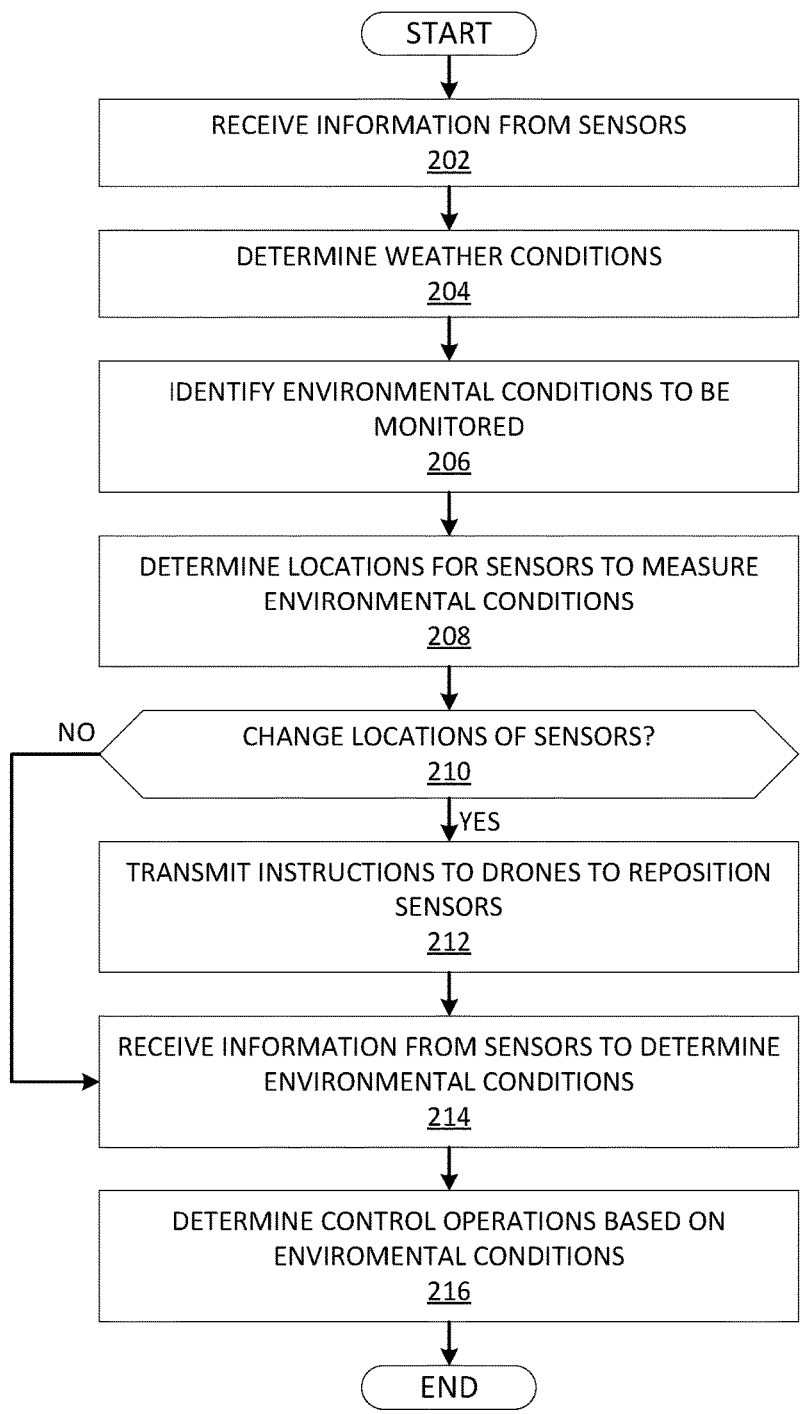
FIG. 2 depicts an exemplary flowchart of a method 500 illustrating the operations of a location program 136 incorporated in the sensor positioning system 100 in coordinating the sensor positioning system 100, in accordance with the exemplary embodiments.

FIG. 2 depicts an exemplary flowchart of a method 200 illustrating the operations of the condition program 134 and the location program 136 incorporated in the sensor positioning system 100, in accordance with the exemplary embodiments. The method 200 may relate to operations that are performed by the condition program 134 and the location program 136 in positioning the sensors 110 via the drones 120. The method 200 will be described from the perspective of the positioning server 130.

The positioning server 130 may receive information from the sensors 110 (step 202). The sensors 110 may already be positioned in the area that is being monitored. For example, the sensors 110 may include weather sensors and environmental sensors that measure weather parameters and environmental parameters, respectively, that were strategically positioned during a previous iteration. In another example, the sensors 110 may be positioned at a default or initial position that serves as a standard positioning of the sensors 110. Using the current positions of the sensors 110, the positioning server 130 may receive the measurements for weather parameters and environmental parameters of the area. In this way, the positioning server 130 may receive an initial sensor feed that is used as a basis for subsequent processing.

The positioning server 130 may determine the weather conditions (step 204). As noted above, the exemplary embodiments may utilize the weather conditions as a basis to determine an impact on environmental conditions. Based on the initial sensor feed, the positioning server 130 may determine the weather conditions using the weather parameters that have been measured by the sensors 110. Through various training techniques and utilizing historical information, the positioning server 130 may be configured to take the weather parameters as in input to determine the weather conditions. The positioning server 130 may identify the environmental conditions to be monitored (step 206). Based on the initial sensor feed, the positioning server 130 may also determine which of the environmental conditions may be present in the area and their likelihood of being impacted by the weather conditions.

The positioning server 130 may determine locations for the sensors 110 to measure the environmental conditions (step 208). Based on the determined weather conditions and the identified environmental conditions, the positioning server 130 may determine which of the sensors 110 may be required to measure the environmental conditions and a location in which these sensors 110 are to be positioned in the area such that the environmental parameters that are measured are done in a very granular manner. Using various training techniques and utilizing historical information, the positioning server 130 may be configured to take the weather conditions and the environmental conditions based on the initial sensor feed as an input to determine the locations for the sensors 110.

The positioning server 130 may determine whether to change the locations of the sensors 110 (decision 210). As the sensors 110 are already positioned in the area, the sensors 110 currently occupy a location in the area. Depending on the type of the sensors 110 and their current location, the sensors 110 may potentially already be in an optimal location to measure the environmental parameters at a very granular level. However, the sensors 110 may also be in a less than optimal location from which the sensors 110 are to be moved. As a result of the locations of the sensors 110 changing (decision 210, "YES" branch), the positioning server 130 may transmit instructions to the drones 120 to reposition the sensors 110 (step 212). The instructions may include an identity of the sensor 110 (e.g., more than one sensor 110 may be co-located so an identity may uniquely identify the sensor 110), a current location of the sensor 110, and an updated location of the sensor 110. The drone 120 may collect the sensor 110 and reposition from the current location to the updated location.

As a result of the locations of the sensors 110 being maintained (decision 210, "NO" branch) or once the sensors 110 have been repositioned (step 212), the positioning server 130 may receive information from the sensors 110 to determine the environmental conditions (step 214). As the sensors 110 are now positioned at the appropriate location to measure the environmental parameters at a very granular level, the positioning server 130 may receive the sensor feed including these environmental parameters to determine the environmental conditions that are being experienced in the area or the particular portion of the area where the sensor 110 is located. The determining of the environmental conditions may provide an input as to the proper control operation that is to be used. Accordingly, the positioning server 130 may determine one or more control operations to be applied to the area based on the environmental conditions (step 216).

The exemplary embodiments are configured to position a plurality of sensors in an area. The exemplary embodiments provide a context aware dynamic positioning system for the sensors such that weather conditions and/or environmental conditions may be determined based on weather parameters and environmental parameters that are measured with a very granular level. By determining the weather conditions and the environmental conditions with greater accuracy, the exemplary embodiments may further determine an appropriate control operation to be applied to the area where the area utilizes the control operation to control one of the environmental conditions.

Figure 3:
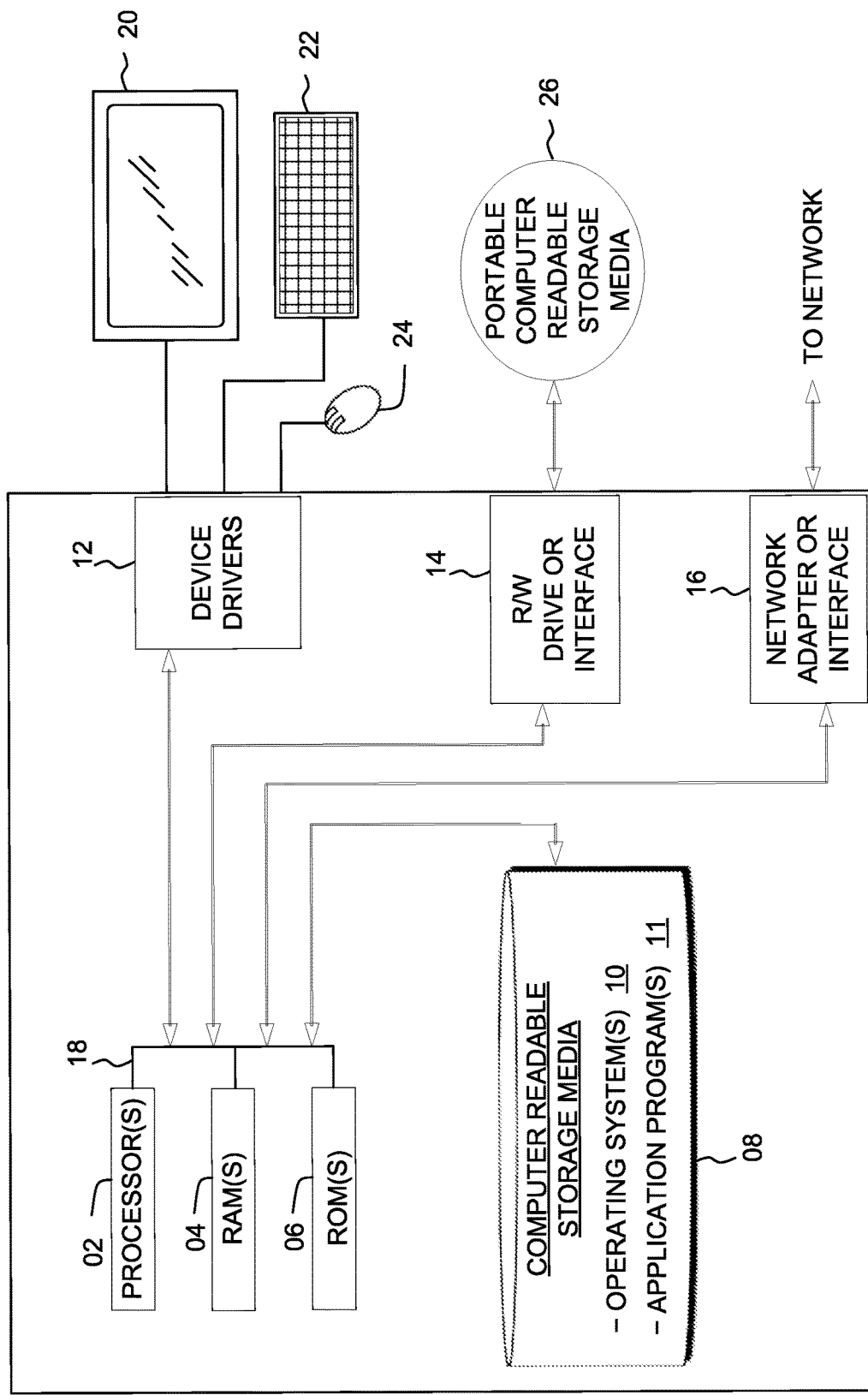
FIG. 3 depicts an exemplary block diagram depicting the hardware components of the sensor positioning system 100 of FIG. 1, in accordance with the exemplary embodiments.

FIG. 3 depicts a block diagram of devices within the sensor positioning system 100 of FIG. 1, in accordance with the exemplary embodiments. It should be appreciated that FIG. 3 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
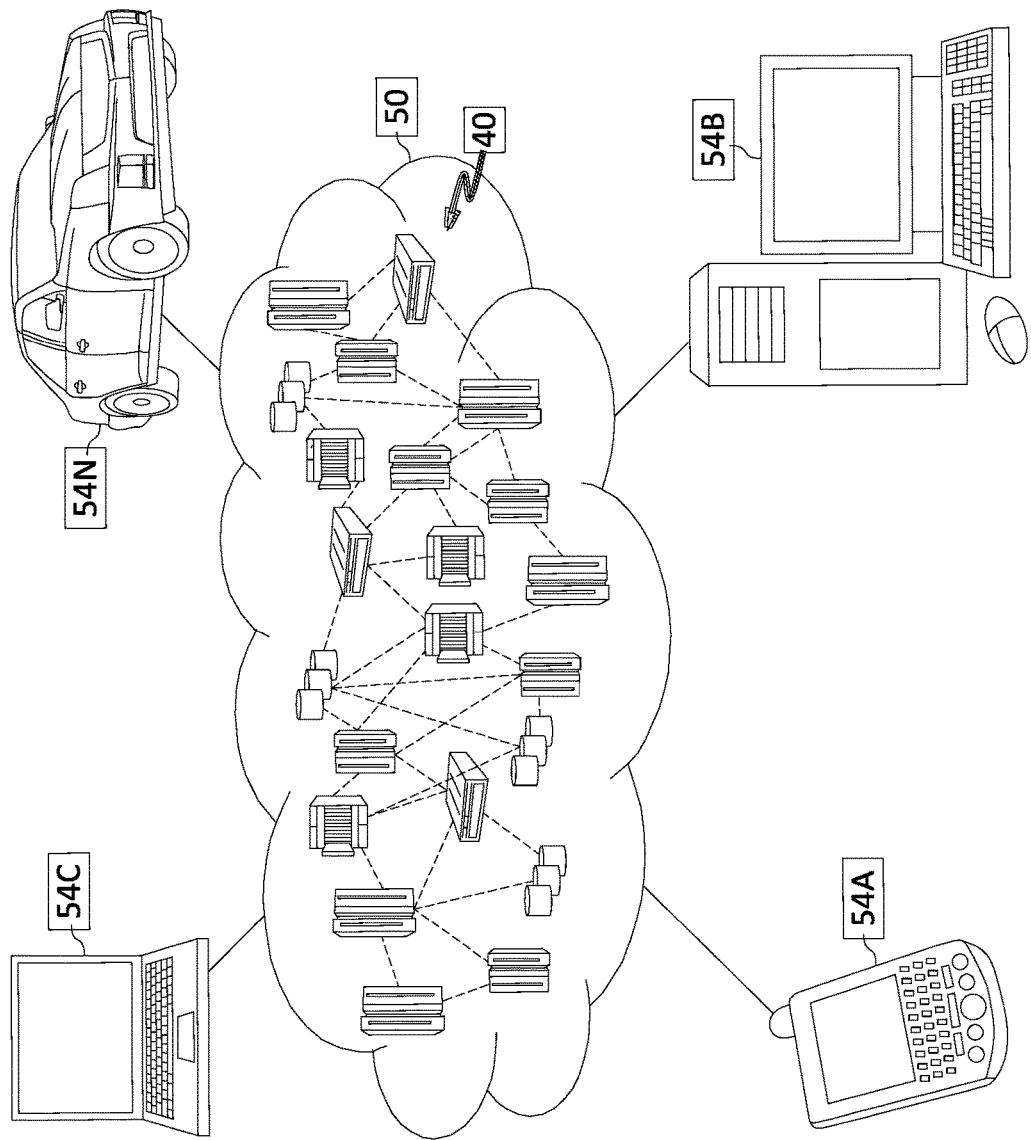
FIG. 4 depicts a cloud computing environment, in accordance with the exemplary embodiments.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Figure 5:
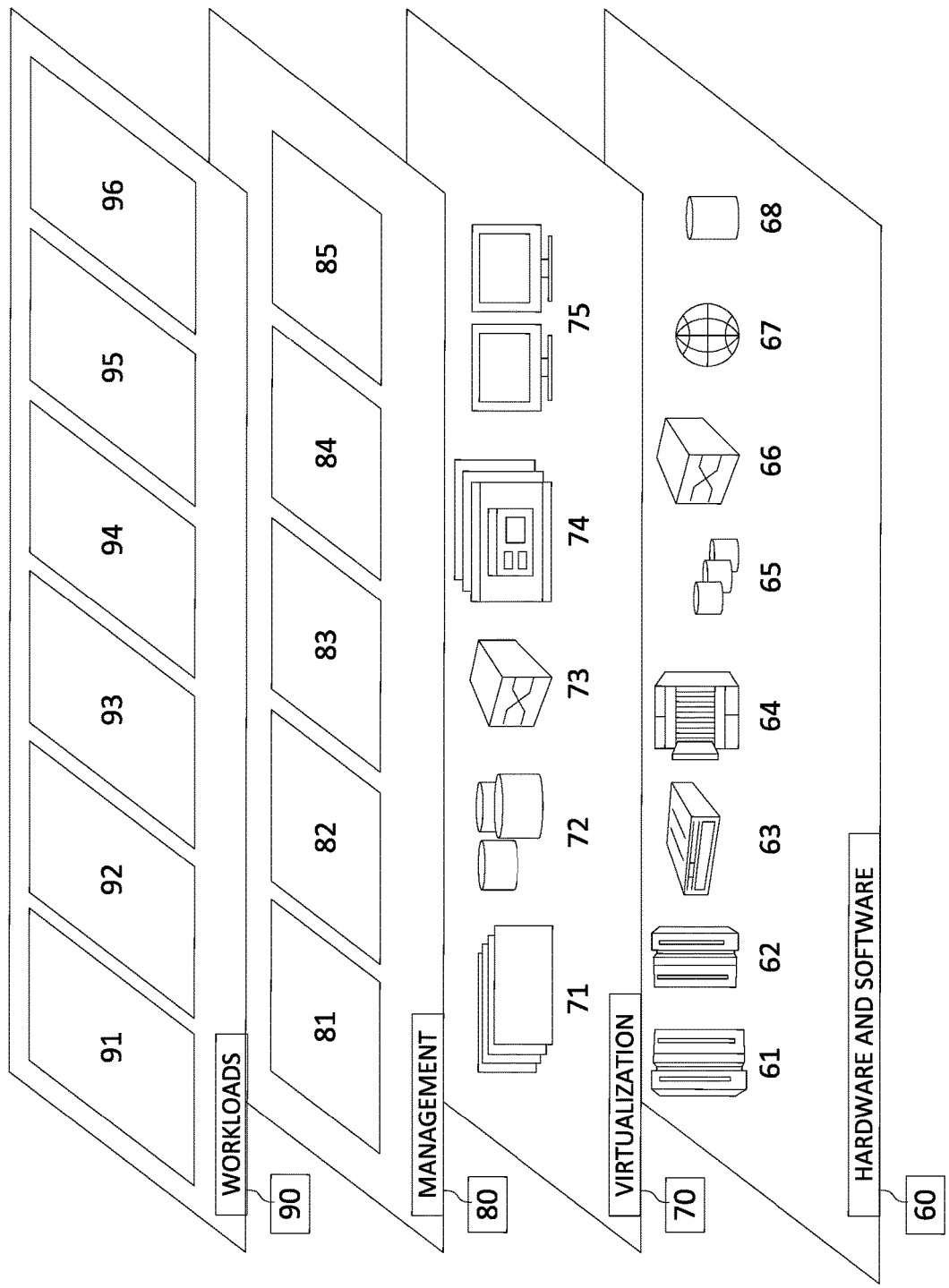
FIG. 5 depicts abstraction model layers, in accordance with the exemplary embodiments.

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 include hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and position processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for positioning a plurality of sensors in an area, the method comprising:
   receiving data from the sensors that are each positioned at a respective first location, the data indicative of weather parameters and environmental parameters;
   determining weather conditions and an environmental condition of the area based on the weather parameters and the environmental parameters;
   determining an impact to the environmental condition by the weather conditions;
   determining a second location for at least one of the sensors to generate further environmental parameters with an increased granular level based on the impact to the environmental condition; and
   transmitting instructions to a delivery robot to move the at least one of the sensors to the second location.

2. The computer-implemented method of claim 1, further comprising:
   receiving the further environmental parameters;
   determining a further environmental condition based on the further environmental parameters; and
   determining a control operation based on the further environmental condition, the control operation configured to reduce a severity of the further environmental condition.

3. The computer-implemented method of claim 1, further comprising:
   determining a type of the sensors to measure the further environmental parameters at the second location based on the environmental parameters.

4. The computer-implemented method of claim 1, further comprising:
   gathering historical weather parameters, historical environmental parameters, historical weather conditions, and historical environmental conditions;
   generating training data from which the impact is determined and the second location is determined.

5. The computer-implemented method of claim 4, wherein the training data indicates at least one correlation between the weather conditions and the environmental condition.

6. The computer-implemented method of claim 1, wherein the weather conditions are indicative of a wind factor and the environmental condition is indicative of a particle concentration.

7. The computer-implemented method of claim 1, wherein the delivery robot is a drone.

8. A coordination server for positioning a plurality of sensors in an area, the coordination server comprising:
   one or more computer processors, one or more computer-readable storage media, and program instructions stored on the one or more of the computer-readable storage media for execution by at least one of the one or more processors capable of performing a method, the method comprising:
   receiving data from the sensors that are each positioned at a respective first location, the data indicative of weather parameters and environmental parameters;
   determining weather conditions and an environmental condition of the area based on the weather parameters and the environmental parameters;
   determining an impact to the environmental condition by the weather conditions;
   determining a second location for at least one of the sensors to generate further environmental parameters with an increased granular level based on the impact to the environmental condition; and
   transmitting instructions to a delivery robot to move the at least one of the sensors to the second location.

9. The coordination server of claim 8, wherein the method further comprises:
   receiving the further environmental parameters;
   determining a further environmental condition based on the further environmental parameters; and
   determining a control operation based on the further environmental condition, the control operation configured to reduce a severity of the further environmental condition.

10. The coordination server of claim 8, wherein the method further comprises:
    determining a type of the sensors to measure the further environmental parameters at the second location based on the environmental parameters.

11. The coordination server of claim 8, wherein the method further comprises:
    gathering historical weather parameters, historical environmental parameters, historical weather conditions, and historical environmental conditions;

generating training data from which the impact is determined and the second location is determined.

12. The coordination server of claim 11, wherein the training data indicates at least one correlation between the weather conditions and the environmental condition.

13. The coordination server of claim 8, wherein the weather conditions are indicative of a wind factor and the environmental condition is indicative of a particle concentration.

14. The coordination server of claim 8, wherein the delivery robot is a drone.

15. A system, comprising:
a plurality of sensors each positioned at a respective first location in an area, the sensors configured to generate data indicative of weather parameters and environmental parameters;
at least one delivery robot configured to transport the sensors; and
a positioning server configured to position the sensors in the area, the positioning server configured to receive the data from the sensors, the positioning server configured to determine weather conditions and an environmental condition of the area based on the weather parameters and the environmental parameters, the positioning server configured to determine an impact to the environmental condition by the weather conditions, the positioning server configured to determine a second location for at least one of the sensors to generate further environmental parameters with an increased granular level based on the impact to the environmental condition, the positioning server configured to transmit instructions to the at least one delivery robot to move the at least one of the sensors to the second location.

16. The system of claim 15, wherein the at least one sensor is configure to generate further data indicative of the further environmental parameters at the second location, and wherein the positioning server is further configured to receive the further environmental parameters, the positioning server is further configured to determine a further environmental condition based on the further environmental parameters, the positioning server is further configured to determine a control operation based on the further environmental condition, the control operation configured to reduce a severity of the further environmental condition.

17. The system of claim 15, wherein the positioning server is further configured to determine a type of the sensors to measure the further environmental parameters at the second location based on the environmental parameters.

18. The system of claim 15, wherein the positioning server is further configured to gather historical weather parameters, historical environmental parameters, historical weather conditions, and historical environmental conditions, and the positioning server is further configured to generate training data from which the impact is determined and the second location is determined.

19. The system of claim 18, wherein the training data indicates at least one correlation between the weather conditions and the environmental condition.

20. The system of claim 15, wherein the weather conditions are indicative of a wind factor and the environmental condition is indicative of a particle concentration.

* * * * *